US012653384B2

(12) United States Patent
Matthison-Hansen et al.

(10) Patent No.: US 12,653,384 B2
(45) Date of Patent: Jun. 16, 2026

(54) ARTICULATED BENDING SECTION BODY FOR AN INSERTION ENDOSCOPE

(71) Applicant: AMBU A/S, Ballerup (DK)

(72) Inventors: Kaspar Mat Matthison-Hansen, Helsingør (DK); Günter Wilhelm Schütz, Augsburg (DE); Thomas Bachgaard Jensen, Copenhagen V (DK)

(73) Assignee: AMBU A/S, Ballerup (DK)

( * ) Notice: Subject to any disclaimer, the term of this patent is extended or adjusted under 35 U.S.C. 154(b) by 462 days.

(21) Appl. No.: 17/921,570

(22) PCT Filed: Apr. 22, 2021

(86) PCT No.: PCT/DK2021/050125
§ 371 (c)(1),
(2) Date: Oct. 26, 2022

(87) PCT Pub. No.: WO2021/219181
PCT Pub. Date: Nov. 4, 2021

(65) Prior Publication Data
US 2023/0165445 A1 Jun. 1, 2023

(30) Foreign Application Priority Data

Apr. 27, 2020 (DK) ........................... PA 2020 70264

(51) Int. Cl.
| | |
|---|---|
| *A61B 1/008* | (2006.01) |
| *A61B 1/005* | (2006.01) |
| *A61B 1/31* | (2006.01) |

(52) U.S. Cl.
CPC ............ *A61B 1/008* (2013.01); *A61B 1/0055* (2013.01); *A61B 1/0057* (2013.01); *A61B 1/31* (2013.01)

(58) Field of Classification Search
CPC ..... A61B 1/008; A61B 1/0055; A61B 1/0057; A61B 1/31
See application file for complete search history.

(56) References Cited

U.S. PATENT DOCUMENTS

| | | | |
|---|---|---|---|
| 3,557,780 A * | 1/1971 | Sato | A61B 1/0055 |
| | | | 600/141 |
| 6,503,194 B2 | 1/2003 | Pauker | |

(Continued)

FOREIGN PATENT DOCUMENTS

JP 2005-261513 A 9/2005

OTHER PUBLICATIONS

First technical report and search opinion in Danish Patent Application No. PA 2020 70264, Jul. 27, 2020, 9 pgs.

(Continued)

*Primary Examiner* — Michael J Carey
*Assistant Examiner* — Megan Elizabeth Monahan
(74) *Attorney, Agent, or Firm* — Faegre Drinker Biddle & Reath LLP

(57) ABSTRACT

An endoscope with an articulated bending section body (1) including a number of segments including a proximal segment (2), a distal segment (3) and a number of intermediate segments (4, 4', 4*i*) arranged between the proximal segment (2) and the distal segment (3). Each intermediate segment (4, 4', 4*i*) comprises at least one through passage for a pull-wire (7). The intermediate segments include (4, 4', 4*i*) at least one interface segment (4*i*) adapted to receive and retain the distal end of a tube (8) surrounding the at least one pull-wire (7).

14 Claims, 5 Drawing Sheets

(56) References Cited

U.S. PATENT DOCUMENTS

Figures 1, 2:
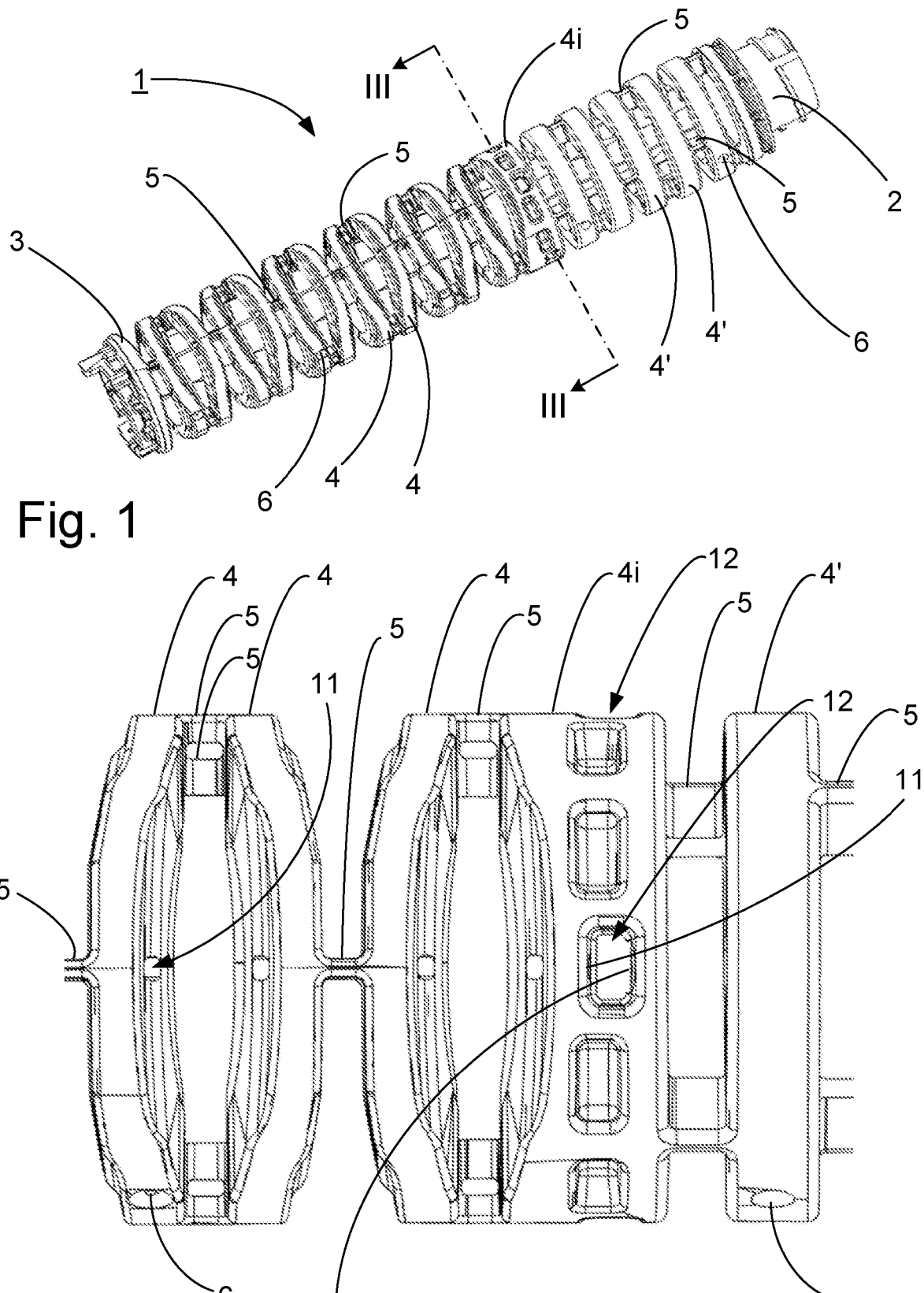

| | | | |
|---|---|---|---|
| 8,052,597 | B2 | 11/2011 | Boulais |
| 8,702,595 | B2 * | 4/2014 | Ueki .................... A61B 1/0057 |
| | | | 600/149 |
| 8,790,250 | B2 | 7/2014 | Petersen et al. |
| 9,968,241 | B2 | 5/2018 | Iuel |
| 10,029,071 | B2 * | 7/2018 | Hannon .................. B29C 48/03 |
| 10,226,185 | B2 * | 3/2019 | Ranganathan .... A61M 25/0051 |
| 10,321,804 | B2 | 6/2019 | Jacobsen et al. |
| 10,441,746 | B2 * | 10/2019 | Besselink ........... A61M 25/104 |
| 11,109,745 | B2 | 9/2021 | Matthison-Hansen |
| 11,357,392 | B2 | 6/2022 | Matthison-Hansen et al. |
| 11,471,031 | B2 | 10/2022 | Jensen |
| 2003/0069522 | A1 * | 4/2003 | Jacobsen ........... A61M 25/0051 |
| | | | 600/585 |
| 2005/0065404 | A1 * | 3/2005 | Moriyama ............. A61B 1/018 |
| | | | 600/104 |
| 2005/0131279 | A1 * | 6/2005 | Boulais ................ A61B 1/0016 |
| | | | 600/141 |
| 2009/0099420 | A1 | 4/2009 | Woodley et al. |
| 2009/0105542 | A1 | 4/2009 | Kitagawa et al. |
| 2009/0234186 | A1 * | 9/2009 | Lin ...................... A61B 1/2736 |
| | | | 600/113 |
| 2010/0094090 | A1 * | 4/2010 | Mejia ................... A61B 1/0014 |
| | | | 600/156 |
| 2010/0217082 | A1 * | 8/2010 | Ito ...................... G02B 23/2476 |
| | | | 600/121 |
| 2012/0265007 | A1 | 10/2012 | Moriyama et al. |
| 2013/0261396 | A1 * | 10/2013 | Boulais ............. A61B 1/00011 |
| | | | 600/142 |
| 2014/0165772 | A1 | 6/2014 | Okazaki |
| 2020/0000322 | A1 | 1/2020 | Belson |
| 2020/0100648 | A1 | 4/2020 | Jensen |
| 2020/0113412 | A1 | 4/2020 | Jensen |
| 2020/0113415 | A1 | 4/2020 | Kristensen |
| 2020/0196835 | A1 | 6/2020 | Qvist et al. |
| 2021/0137354 | A1 | 5/2021 | Bob et al. |
| 2021/0212783 | A1 | 7/2021 | Kowshik |
| 2021/0393113 | A1 | 12/2021 | Matthison-Hansen |

OTHER PUBLICATIONS

International Preliminary Report on Patentability received for PCT Patent Application No. PCT/DK2021/050125, mailed on Nov. 10, 2022, 7 pages.

International Search Report and Written Opinion received for PCT Patent Application No. PCT/DK2021/050125, mailed on Jul. 23, 2021, 9 pages.

* cited by examiner

ARTICULATED BENDING SECTION BODY FOR AN INSERTION ENDOSCOPE

CROSS REFERENCE TO RELATED APPLICATIONS

This application is a National Stage entry under 35 U.S.C. § 371 of International Application No. PCT/DK2021/050125, filed Apr. 22, 2021, which claims priority from and the benefit of Danish Patent Application No. PA 2020 70264, filed Apr. 27, 2020; said applications are incorporated by reference herein in their entirety.

The present disclosure relates to insertion endoscopes in particular to the articulated bending section of such an endoscope.

Insertion endoscopes typically comprises a handle at the proximal end gripped by an operator and a flexible elongated insertion tube terminated at the distal end in a tip part at the end of a highly bendable, e.g. articulated, bending section, controllable by the operator. The tip part normally comprises a visual inspection means such as a camera, and illumination means such as LED's or exit apertures of light fibres and whatever optics is needed in that connection. Electrical wiring for the camera and other electronics such as the LED lighting run along the inside of the elongated insertion tube from the handle to the tip at the distal end. When, as mentioned, the illumination is instead fibre-optic, the optical fibres run along inside of the elongated insertion tube.

Thus, the controllable bending section is normally an articulated section at the distal tip of the elongated insertion tube that can be controlled by the operator via control knobs arranged on the handle. Typically, this control is effected by tensioning or slacking pull-wires also running along the inside of the elongated insertion tube from the articulated tip part to a control mechanism of the handle. Furthermore, a working channel may run along the inside of the elongated insertion tube from the handle to the tip, e.g. allowing liquid to be removed from the body cavity or allowing the insertion of surgical instruments or the like into the body cavity.

Thus, using the controls allows the operator to advance the distal tip of the endoscope to a desired location by means of a series of actions involving inter alia bending the bending section in a desired direction, advancing the elongated insertion tube and turning the elongated insertion tube by turning the handle which is rigidly connected thereto. Negotiating a tortuous path of bends and turns to a location of interest may subject the elongated insertion tube including the distal controllable bending section to substantial forces including compression, torsion, and bending. The main body of the elongated insertion tube is essentially only bendable enough to follow the direction taken by the articulated bending section. In fact, it could be said that it is an essential part of the purpose of the elongated insertion tube to transmit the longitudinal pushing forces and rotary torsional forces from the handle to the distal end of the elongated insertion tube in order to allow these maneuvers.

In some types of endoscopes such as colonoscopes, it is known to provide a dual bending section, comprising a passive bending section proximal to an active bending section, i.e. between the highly flexible active bending section operated by steering wires and the less flexible main tube of a flexible endoscope. The passive bending section improves maneuverability in some clinical settings. In practice, the pull-wires form parts of Bowden cable, i.e. the pull-wires run freely inside a tube which, in turn, is fixed against longitudinal motion with respect to the handle and the insertion tube body.

To provide both a passive and an active bending section the tube is terminated inside the bending section body, so that the free distal end of the pull-wires may bend the active section by pulling on the distal end segment to which they are affixed. This pulling will also compress and bend articulated segments surrounding the tube of the Bowden cable, although not to the same extent because of the tube.

Having to terminate the tube deep inside the bending section body makes the bending section body more complex and, in turn, more complicated to mould as a single item.

Based on the above it is the object of the present disclosure to provide an articulated bending section body for an endoscope than renders itself to easy manufacturing while at the same time allowing termination of the tubes of Bowden cables to terminate within the articulated bending section body.

According to a first aspect of the disclosure this object is achieved by an endoscope comprising an articulated bending section body, said articulated bending section body comprising number of segments including a proximal end segment, a distal end segment and a number of intermediate segments arranged between the proximal segment and the distal segment, where each intermediate segment comprises at least one through passage for a pull-wire, wherein said number intermediate segments comprise at least one interface segment adapted to receive and retain the distal end of a tube surrounding said at least one pull-wire. By providing such a specialized interface segment it becomes readily possible to terminate the tube of the Bowden cable deep inside the articulated bending section body.

According to a second aspect of the invention the object is achieved by system comprising an endoscope according to the first aspect of the invention and a display unit connectable to said endoscope.

According to a preferred embodiment of the first aspect of the disclosure, the endoscope comprises said tube surrounding said at least one pull-wire and said interface segment comprises a through bore in which the diameter of the bore at its distal end is smaller than the outer diameter of the tube it is adapted to receive and in which the diameter of the bore at its proximal end is larger than the outer diameter of the tube it is adapted to receive. This will, in particular if the bore comprises a frusto-conical part in which the tube may wedge.

According to a further preferred embodiment of the first aspect of the disclosure, the at least one interface segment comprises an essentially cylindrical body part provided with a number of radially extending recesses. Providing such recesses in the surface provides two advantages when manufacturing the articulated bending section body. The main advantage being that the material dimensions, in particular thicknesses, become more equal over the entire bending section body, but in particular in the interface segment itself. This makes the hot moulded item cool in a more harmonized manner when the item is made by injection moulding, and thus prevents shrinking, warping and other undesired effects. Also, the flow of liquefied plastic material will be more harmonic and better fill the mould during injection.

According to yet a further preferred embodiment of the first aspect of the disclosure, at least one radially extending recess among said number of radially extending recesses is in communication with said through bore. This allows access to the distal end of the tube when mounting the tube during manufacture. It furthermore allows glue or the like to be poured or injected into the recess for further securing the tube with respect to the interface segment.

According to another embodiment of the first aspect of the disclosure, at least one further recess among said number of radially extending recesses is arranged in parallel with said at least one radially extending recess. This further aids in keeping the material thicknesses equal and furthermore allows the mould parts of mould to be kept relatively simple and easily separable after moulding the articulated bending section body.

This is in particular the case when according to yet another preferred embodiment, according to which said at least one further recess comprises two sides extending as chords in a cross-section of the essentially cylindrical body. This allows for an essentially box shaped recess or a pyramid base shape. Preferably, the chords form an angle of less than 10 degrees, with respect to the radial direction, preferably less than 5 degrees. That is to say a pyramid base shape with so steep sides that it approaches a box shape.

According to a further preferred embodiment of the first aspect of the disclosure, a clamping device adapted to receive and retain the distal end of a tube surrounding said at least one pull-wire pair is provided in said radially extending recess. This allows for further fixation of the tube end in the interface member.

According to yet a further preferred embodiment, said clamping device comprises a pair of upright protrusions extend from the bottom of the radially extending recess. These allow elastic clamping of the tube for efficient fixation.

According to another alternative embodiment, the articulated bending section body comprises a clamping device extending in the axial direction of said articulated bending section, said clamping device being adapted to receive and retain the distal end of a tube surrounding said at least one pull-wire pair, in particular an axially extending clamping device comprising a number of protrusions, preferably three, arranged around a pull-wire passage and each extending in said axial direction. This allows the resiliency of the protrusions to clamp the end of the tube in a simple but efficient manner.

According to a further preferred embodiment, the bending section body is a single-piece integrally moulded item. This renders the bending section body highly suitable for low-cost mass production, and hence for the use in disposable endoscopes.

Figures 3, 4:
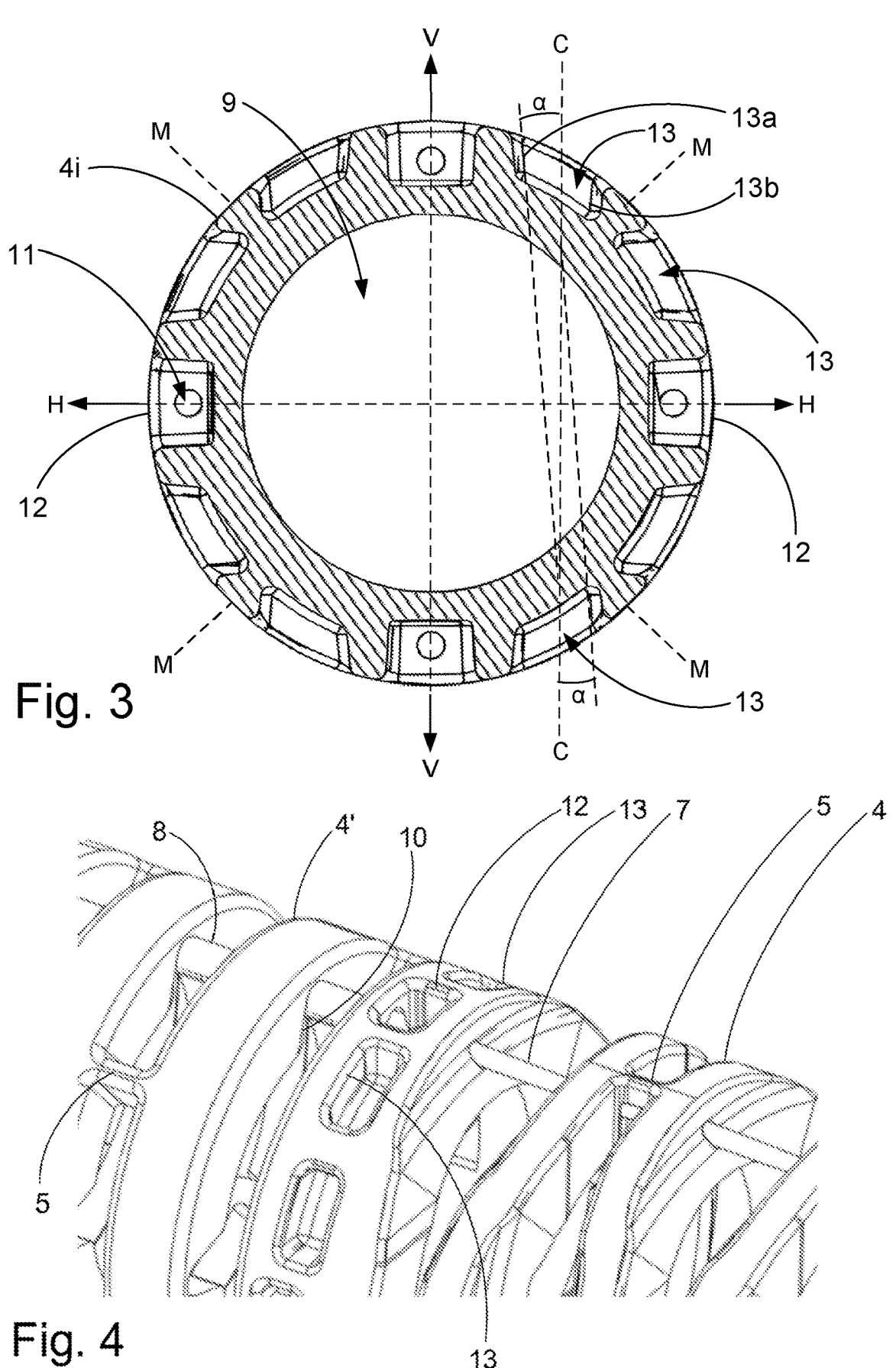
Figure 5:
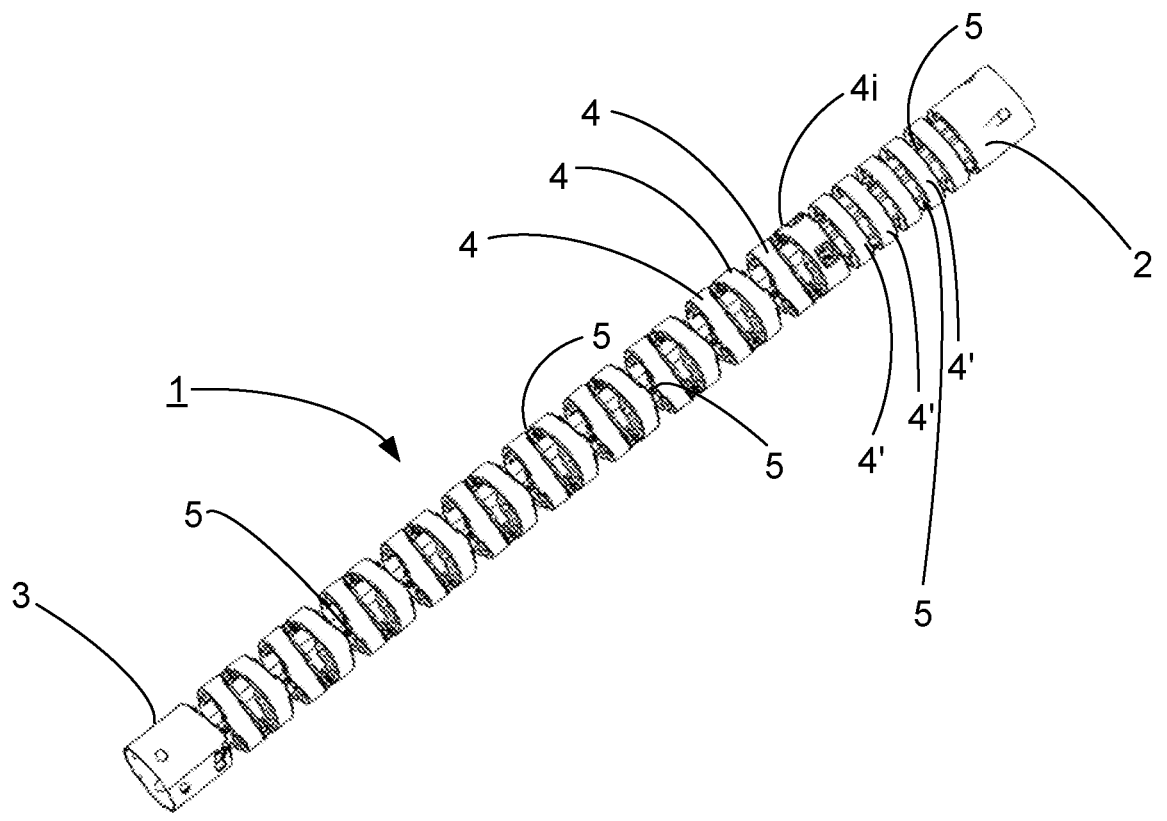
Figure 6:
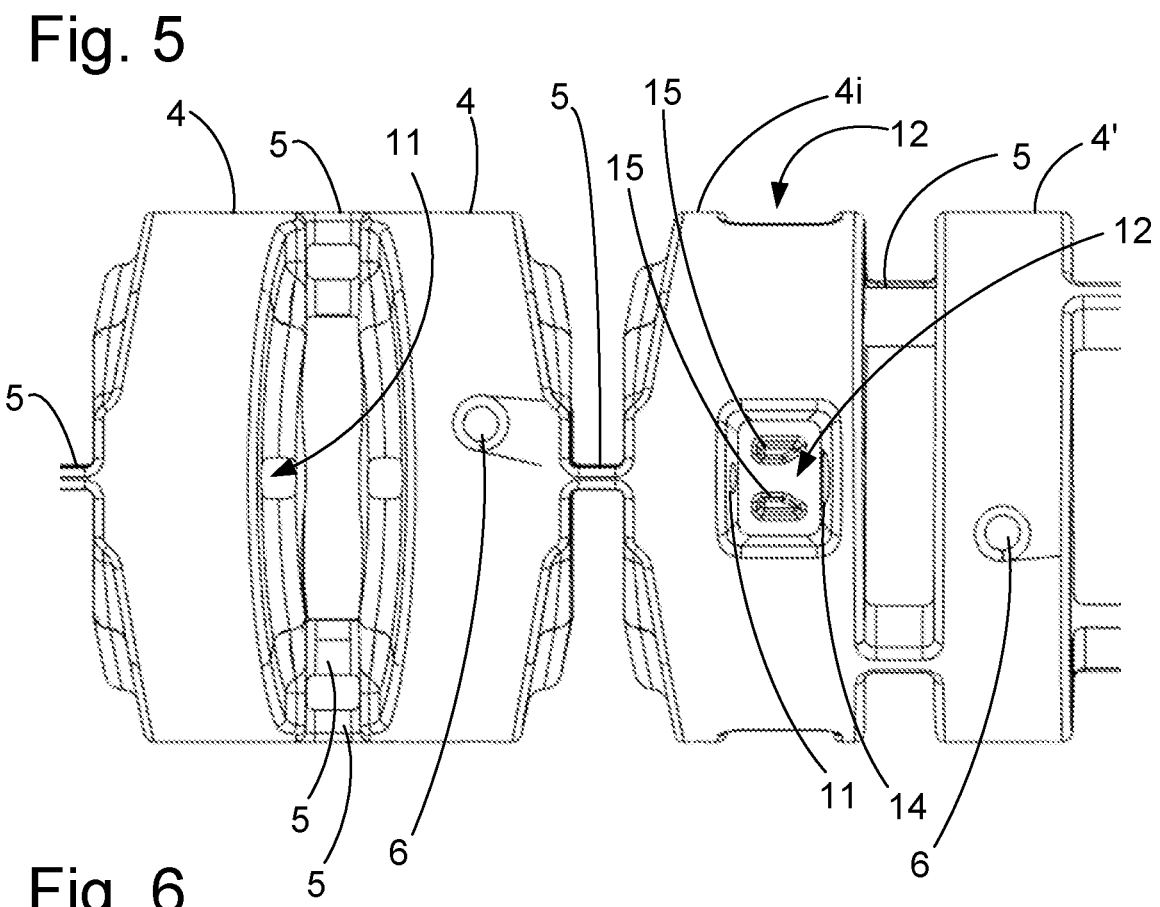
Figure 7:
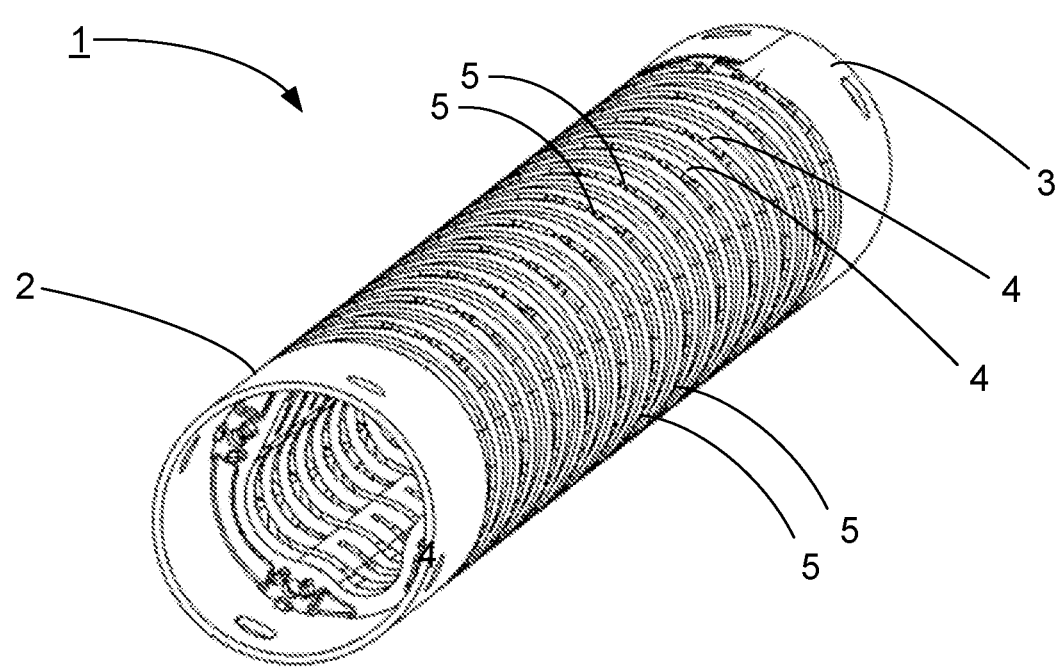
Figure 8:
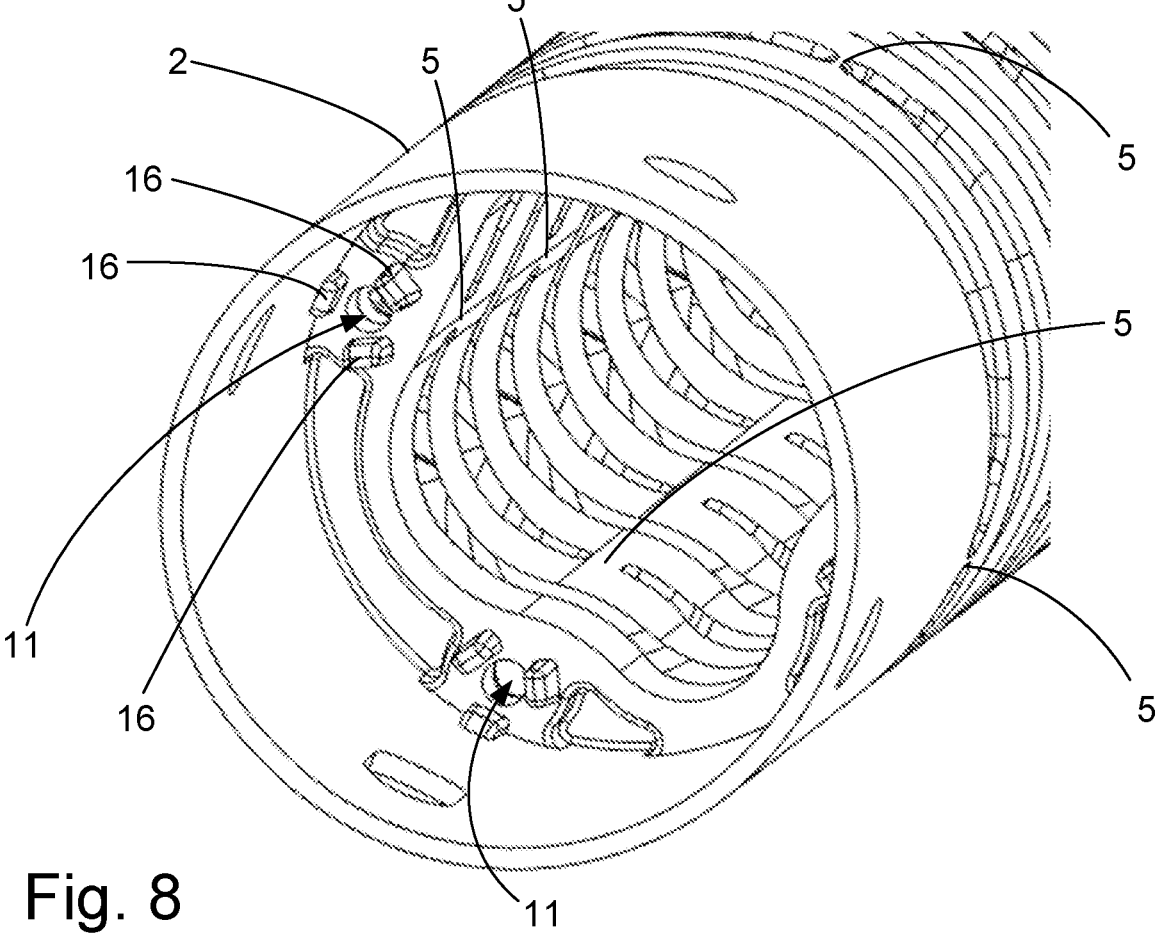
Figure 9:
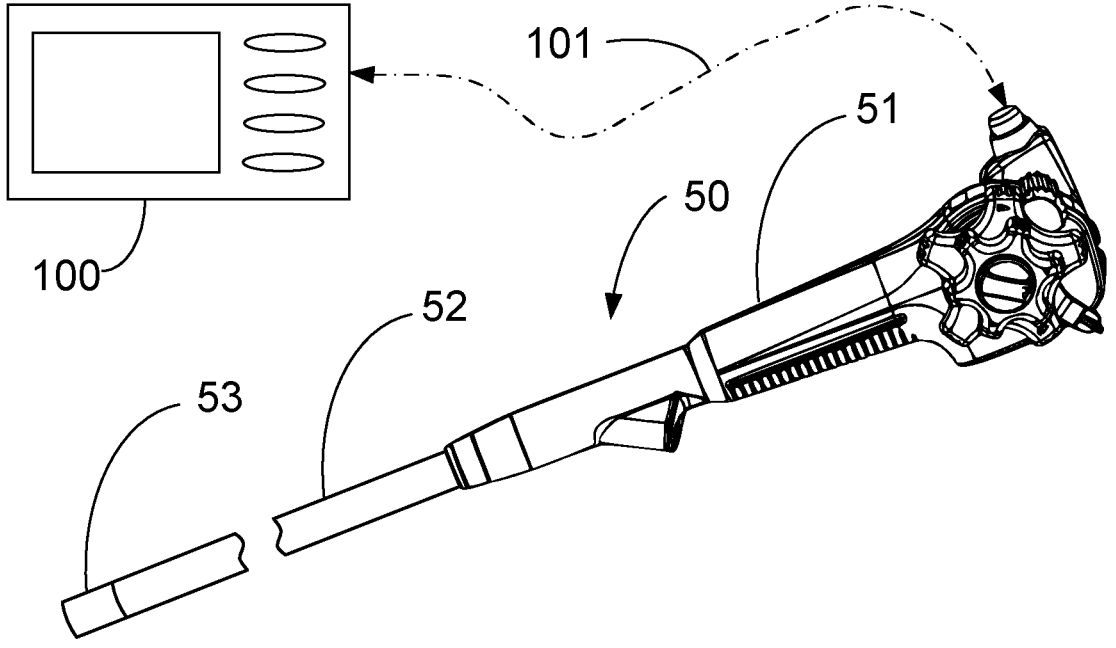

The disclosure will now be made in greater detail based on nonlimiting exemplary embodiments and with reference to the schematic drawings on which:

FIG. 1 shows an isometric view of a first embodiment of an articulated bending section body according to the disclosure, FIG. 2 shows a partial top plan view of an interface segment of the articulated bending section body of FIG. 1 and a few adjacent segments, FIG. 3 shows a cross-section of the interface segment taken along the line III-III of FIG. 1, FIG. 4 shows a partial isometric view of the interface segment of FIG. 1 with mounted a Bowden cable comprising pull-wire and surrounding tube, FIG. 5 shows an isometric view of a second embodiment of an alternative articulated bending section body according to the disclosure, and FIG. 6 shows a partial top plan view of the interface segment of the articulated bending section body of FIG. 5 and a few adjacent segments, FIG. 7 shows an alternative embodiment of an articulated bending section body, FIG. 8 shows the distal end segment of the articulated bending section body of FIG. 7 in greater detail, and FIG. 9 shows a medical system comprising a display unit and an endoscope incorporating the articulated bending section body.

Turning first to FIG. 9 a system comprising a display device 100 and an endoscope 50 connectable to the display device 100 by means of a cable 101 or a wireless connection is shown. The endoscope 50 comprises a handle 51 at the proximal end and an insertion tube 52 connected to a bending section 53 forming part of the distal end of the endoscope 50. The bending section 53 comprises an articulated bending section body 1. The bending section body 1 is not visible in FIG. 9 because it is covered by a thin external sheath 13. Reference is therefore now made to FIGS. 1 to 8.

In FIG. 1 a first embodiment of an articulated bending section body 1 according to the disclosure is shown. The articulated bending section body 1 comprises a proximal end segment 2 and a distal end segment 3. Between the proximal end segment 2 and the distal end segment 3 a number of intermediate segments 4, 4', 4i are arranged. The intermediate segments 4, 4', 4i are interconnected by means of hinge members 5, such as foil hinges. The intermediate segments 4 are preferably largely identical or may, as is the case in the embodiment, comprise sets of largely identical intermediate segments 4, 4'. More specifically, the set of intermediate segments 4 closer to the distal end segment 3 in FIG. 1 differ from the set of intermediate segments 4' closer to the proximal end segment 2. Apart from that the intermediate segments 4 in each set may differ in immaterial details such as the presence or location of remains of moulding inlets 6, ejector marks etc. from manufacture, and the fact that each of them are turned by 90 degrees with respect to its neighbor. Also, as will be noted in this embodiment the rotational symmetry is such that turning an intermediate segment 4 by 90 degrees makes it correspond to its own mirror image. Furthermore, according to the disclosure the two sets of intermediate segments 4, 4' are separated by a specialized intermediate segment, in the following referred to as interface segment 4i.

The interface segment 4i inter alia differs from the other segments 2, 3, 4, 4' in that it is adapted to receive and retain the distal end of a tube surrounding a pull-wire, cf. FIG. 4. This difference and other details to be described below could, however, also be implemented in the proximal segment 2. As can be seen in FIG. 4 a pull-wire 7 extends through the bending section body 1. Although in FIG. 4 only a few intermediate segments 4, 4' on either side of the interface segment 4i is shown, the skilled person will understand that the pull-wire 7 extends also through the proximal end segment 2 and therefrom through all intermediate segments 4, 4' to the distal end segment where it is terminated in a well-known manner allowing it to exert a pull on the distal end segment 3. As can be seen from FIG. 4 a part of the pull-wire 7 is surrounded by a tube 8, so as to be able to provide a Bowden cable. Providing the pull-wire 7 as a Bowden cable furthermore allows the part of the pull-wire 7 surrounded by the tube 8 to simply lie in the central aperture 9 of the proximal end segment 2 and the intermediate segments 4'. This could possibly be in suitable cut-outs 10 in the periphery of the central aperture 9, be it all the way or just in the intermediate segments 4' closest to the interface segment 4i, e.g. for allowing alignment with dedicated apertures 11 for the naked pull-wire 7 through the intermediate segments 4. As can best be seen in FIGS. 2 and 4 these apertures 11 forming the passages for the pull-wires lie essentially in the planes of the hinge members 5, thus de facto splitting each foil hinge in two.

In order to provide the bending section body 1 with a passive and an active bending section part, the tube 8 is terminated in the interface segment 4*i*. As can be seen from FIG. 4 the interface segment 4*i* comprises a radially extending recess 12 in which the tube 8 is terminated. The tube 8 enters the recess 12 through an opening in the proximal side of the interface segment, e.g. a bore 14 adapted in diameter to the tube 8. The tube 8 terminates in the recess 12 and only the pull-wire 7 exits the recess 12, preferably through a smaller diameter bore 11 provided in the distal side of the interface segment 4*i* and adapted to the diameter of the pull-wire 7. The bore 14 may be tapered to frictionally hold the tube 8, but additionally or alternatively the tube may be held by glue or the like poured into the recess 12 upon placement of the tube 8.

Apart from providing access to end of the tube 8 from the exterior of the bending section body 1 during placement and fixation, the recess 12 provides advantages when moulding the bending section body 1, in particular when further recesses 13 are provided in the interface segment 4*i*.

The provision of the recesses reduces the maximum material thickness thereby bringing it closer to the average value. Keeping material thicknesses so close as possible to each other throughout the bending section body, allows for better controllable flow during injection moulding, and subsequently for more equalized cooling of the bending section 1, thereby improving the quality of the moulded bending section body 1.

As can best be seen in FIG. 3 the radially extending recesses 12 are generally symmetrically arranged on either side of a radius (or diameter) defining a symmetry plane along the length of the bending section body 1, in the relaxed, as made, state thereof, i.e. without any external forces action thereupon, and hence also symmetrically with respect to the interface segment 4*i*. In the embodiment of FIG. 3 there are two such symmetry planes indicated by the dashed arrows V-V and H-H. The radially extending recesses 12 are generally box-shaped although the sides may be at a small angle so that there is a slight taper in the inward radial direction. This angle is preferably smaller than 10 degrees, preferably smaller than 5 degrees, with respect to the symmetry plane. Thus, the angle could be approximately or equal to any one of 1, 2, 3, 4, 5, 6, 7, 8, 9 or 10 degrees. The same applies with respect to a cross-sectional plane about which the radially extending recesses 12 may be symmetrical in the longitudinal direction of the bending section body 1. This taper (which academically speaking gives the box-shaped recess 12 a pyramid base shape) aids the release of the moulded bending section body from the mould. The mould is not shown, but merely indicated by dashed lines M indicating where four mould parts surrounding the bending section body 1 separate when retracted in the radial directions of the arrows V-V and H-H after moulding the bending section body 1. The edges of the otherwise box-shaped radially extending recesses 12 may furthermore be chamfered or rounded to further aid in efficiently moulding and releasing the bending section body 1.

To further avoid the material thicknesses from deviating from the desired average value, additional recesses 13 are preferably provided. These additional recesses 13 are asymmetrical as compared to the radially extending recesses 12 in order to allow proper release from the mould when the mould parts are retracted. Thus, the side 13*a* and 13*b* walls are essentially parallel with or at a small angle α to a radial direction V-V or a chord C-C in the essentially circular body of the interface segment 4*i*, as illustrated in the top right-hand corner of FIG. 3. The same would apply likewise to the other seven asymmetrical recesses 13 in FIG. 3, albeit some with respect to the radial direction H-H instead. Preferably the angle α is less than 10 degrees, most preferred less than 5 degrees, such as approximately or equal to any one of 1, 2, 3, 4, 5, 6, 7, 8, 9 or 10 degrees, i.e. corresponding to the angles of the radially extending recesses 12. The bottom of the recesses 13 are preferably curved, ideally circular, to preserve the same thickness or distance to the central aperture 9. The two remaining walls of each recess 13 may also be inclined with respect to a cross-sectional plane, preferably with an angle corresponding to that of the angle α. Each of the additional recesses thus essentially extend in parallel with at least one of the radially extending recesses 12.

FIGS. 5 and 6 shows another embodiment of a bending section body 1 according to the disclosure. The views correspond largely to those of FIGS. 1 and 2 and same reference numerals have been used for same or equivalent features. Accordingly, the bending section body 1 shown in FIGS. 5 and 6 also comprises a proximal end segment 2 a distal end segment 3 and a number of intermediate segments 4, 4' and 4*i*, interconnected by hinge members. However, in the interface segment 4*i* only radially extending recesses 12 are provided. Addition of further recesses corresponding to the asymmetrical recesses 13 of the embodiment of FIGS. 1 to 4 is, however, not excluded. Rather, the skilled person will understand that this and other features are interchangeable between both embodiments. Thus, angles and similar of the walls of the radially extending recesses 12 may be the same. In fact, the major difference between the radially extending recesses 12 of FIGS. 1 to 4 reside in the provision of an additional clamping member in the bottom of the radially extending recess 12. In the preferred embodiment, two uprights 15 are provided with a spacing suitable for clamping the end of the tube 8 to be terminated in the radially extending recess. This provides additional securing of the tube 8 in the interface segment 4*i*, as compared to the embodiment of FIGS. 1 to 4. Thus, the end of the tube 8 may during assembly be wedged into the gap between the two uprights and held there by a combination of its own resiliency and spring forces from the uprights 15. It may of course be further secured by means of glue or the like.

Although the present disclosure has now been described based on detailed embodiments, the skilled person will understand that it is well possible to deviate from such detail while still remaining within the scope of the claims. In particular features are interchangeable and some features may even be omitted. Although the outset of this disclosure is the provision of a bending section body allowing for both passive and active bending it is, in particular it is envisaged that the features of the interface segment such as those relating to the moulding, could be implemented solely in the proximal section of a bending section.

Accordingly, in FIG. 7 an alternative bending section body with features interchangeable with the already described bending section bodies of the disclosure is shown. Corresponding features and interchangeable features have the same reference numerals as in the previously bending section bodies. Thus, as can be seen the bending section body comprises a proximal end segment 2, a distal end segment 3 and a number of intermediate segments 4, where all segments are connected to a neighboring segment by means of hinge members 5, in particular foil hinges moulded integrally in one piece with the remainder of the bending section body. In this respect is of course to be understood that the term foil as used in foil hinges, does not imply an extended thin membrane, but just a short and thin bendable bridge between segments 2, 3, 4, 4', 4*i*.

As can better be seen in the detailed view of the proximal end segment 2 in FIG. 8 the distal end segment as well as the intermediate segments comprise through passages 11 such as dedicated apertures for pull-wires of a Bowden cable. In the embodiment shown there are four sets of through passages through the proximal end segment and the intermediate segments. These passages 11 preferably coincide with the planes of the hinge members 5, so that each foil hinge is de facto split in two, similarly to the previously described bending section bodies, cf. FIGS. 2 and 4.

To secure the distal end of the outer tube of the Bowden cable the though passage 11 of the relevant segment, be it the interface segment 4*i* as described above or, as shown in FIG. 8, the proximal end segment 2, the relevant segment comprises a number of axially extending protrusions 16, i.e. extending in parallel with a centre axis of the bending section body or the axes corresponding to the pull-wires when straight. Preferably, there are three protrusions surrounding each dedicated aperture 11. These protrusions 16 may all be free-standing or one or more may be integrally formed with the outer wall of the segment. Thus, the end of the tube 8 may during assembly be wedged into the gap between the three protrusions 16 and held there by a combination of its own resiliency and spring forces from the protrusions 16. It may of course be further secured by means of glue or the like. More than three protrusions 16 surrounding the dedicated aperture may of course be used for each tube 8.

What is claimed is:

1. An endoscope comprising:
   an articulated bending section body comprising a single-piece integrally molded item comprising a passive section, an active section, and an interface segment between the passive section and the active section, the active section being distal of the passive section, the single-piece integrally molded item including:
   a proximal segment;
   a distal segment; and
   intermediate segments, some of the intermediate segments arranged in the active section and some of the intermediate segments arranged in the passive section;
   wherein the interface segment comprises:
   a proximal surface facing the passive section,
   a distal surface facing the active section,
   a circumferential surface between the proximal surface and the distal surface,
   a pull-wire through-bore extending longitudinally between the proximal surface and the distal surface and comprising a proximal end and a distal end, the proximal end configured to receive therethrough a pull-wire and a distal end of a tube surrounding the pull-wire, and the distal end of the pull-wire through-bore configured to receive therethrough the pull-wire and to prevent passage of the tube,
   blind holes extending radially inward from the circumferential surface between the proximal surface and the distal surface.

2. The endoscope of claim 1, further comprising the tube and the pull-wire.

3. The endoscope of claim 1, one of the blind holes extends to, and is in communication with, the pull-wire through-bore.

4. The endoscope of claim 1, wherein at least one of the blind holes comprises two sides as chords in a cross-section of a cylindrical body of the interface segment.

5. The endoscope of claim 4, wherein the chords form an angle of less than 10 degrees, with respect to a radial direction.

6. The endoscope of claim 5, wherein the chords form an angle of less than 5 degrees, with respect to the radial direction.

7. The endoscope of claim 1, wherein the interface segment further comprises a clamping device provided in one of the blind holes, the clamping device configured to receive and retain the distal end of the tube surrounding the pull-wire.

8. The endoscope of claim 7, wherein the clamping device comprises a pair of upright protrusions.

9. The endoscope of claim 1, wherein one of the blind holes comprises a bottom opposite an outer aperture and a pair of upright protrusions extending outward from the bottom, the pair of upright protrusions configured to receive and retain the distal end of the tube surrounding the pull-wire.

10. The endoscope of claim 1, further comprising an axially extending clamping device configured to receive and retain the distal end of the tube surrounding the pull-wire.

11. The endoscope of claim 10, wherein the axially extending clamping device comprises axially extending protrusions arranged around the pull-wire through-bore.

12. The endoscope of claim 1, the proximal segment further comprising a through-passage for the pull-wire and axially extending protrusions configured to receive and retain the distal end of the tube surrounding the pull-wire, the axially extending protrusions arranged around the through-passage for the pull-wire.

13. The endoscope of claim 1, interface segment further comprises axially extending protrusions configured to receive and retain the distal end of the tube surrounding the pull-wire, the axially extending protrusions arranged around the pull-wire through-bore.

14. A system comprising the endoscope according to claim 1 and a display unit connectable to said endoscope.

* * * * *